United States Patent [19]

Cölln et al.

[11] 4,123,478
[45] Oct. 31, 1978

[54] PREPARATION OF O,O-DIMETHYL-O-(2,2-DICHLOROVINYL)-THIONOPHOSPHORIC ACID ESTER

[75] Inventors: Reimer Cölln, Wuppertal; Wilhelm Sirrenberg, Sprockhoevel, both of Germany

[73] Assignee: Bayer Aktiengesellschaft, Leverkusen, Germany

[21] Appl. No.: 820,500

[22] Filed: Jul. 29, 1977

[30] Foreign Application Priority Data

Aug. 16, 1976 [DE] Fed. Rep. of Germany ....... 2636786

[51] Int. Cl.$^2$ ............................................. C07F 9/165
[52] U.S. Cl. ..................................... 260/986; 260/957
[58] Field of Search ................................. 260/957, 986

[56] References Cited

U.S. PATENT DOCUMENTS 2,865,943  12/1958  Lorenz ............................ 260/957 X

*Primary Examiner*—Anton H. Sutto
*Attorney, Agent, or Firm*—Burgess, Dinklage & Sprung

[57] ABSTRACT

A process for the preparation of O,O-dimethyl-O-(2,2-dichlorovinyl)-thionophosphoric acid ester of the formula

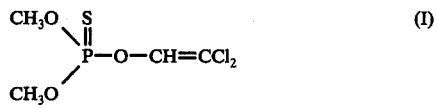

(I)

comprising reacting O,O-dimethyl-1-hydroxy-2,2,2-trichloroethane-thionophosphonic acid ester of the formula

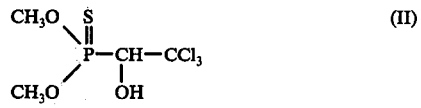

(II)

in isopropanol with a 30–50% aqueous solution of an alkali metal hydroxide, possibly present in a small molar excess.

7 Claims, No Drawings

PREPARATION OF O,O-DIMETHYL-O-(2,2-DICHLOROVINYL)-THIONOPHOSPHORIC ACID ESTER

The present invention relates to a novel process for the preparation of O,O-dimethyl-O-(2,2-dichlorovinyl)-thionophosphoric acid ester, which is known as an insecticide.

A process has already been described, in Belgian Patent Specification No. 839,712, according to which O,O-dimethyl-O-(2,2-dichloro-vinyl)-thionophosphoric acid ester can be obtained when O,O-dimethyl-1-hydroxy-2,2,2-trichloroethane-thionophosphonic acid ester is treated with a solution of an equivalent amount of an alkali metal alcoholate or alkali metal carbonate or a solution of an alkali metal hydroxide or alkali metal carbonate in an alcohol, in which case, for this compound, methanol is used as the alcohol in order to avoid trans-esterifications of the two methoxy groups.

A disadvantage of this process is, however, that the use of methanol together with the alkali employed to a certain extent gives rise to the formation of O,O,O-trimethylthionophosphoric acid ester in that partial replacement of the dichlorovinyloxy group, which has just been formed, by the methoxy group takes place.

This undesired side-reaction as a rule leads to a contamination, amounting to up to 5%, of the desired reaction product by O,O,O-trimethylthionophosphoric acid ester, which can be separated off only by expensive fractional distillation. In addition, the side-reaction mentioned lowers the yield by a corresponding amount. There is, therefore, great interest in a process which does not possess such a defect.

The present invention now provides a process for the preparation of O,O-dimethyl-O-(2,2-dichloro-vinyl)-thionophosphoric acid ester, which has the formula

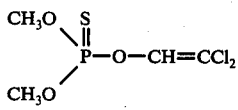

in which O,O-dimethyl-1-hydroxy-2,2,2-trichloroethane-thionophosphonic acid ester, which has the formula

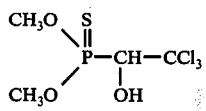

is reacted in an isopropanol solution with a concentrated aqueous solution of one equivalent of an alkali metal hydroxide.

It is to be regarded as extremely surprising, especially because of the presence of aqueous alkali metal hydroxide, that the process according to the invention can lead to an unexpectedly high yield and purity of the end product since, with regard to the state of the art, it would have had to be expected that the use of an aqueous alkali metal hydroxide solution would lead to increased hydrolysis and a reduced yield and purity. The low purity of the reaction product according to Example 2 of Belgian Patent Specification No. 839,712 is to be understood in this sense since, in this case, the reaction was carried out in the presence of water.

The process according to the invention displays a number of advantages. Thus, the high purity of the reaction product that can be achieved, which renders superfluous expensive purification by distillation, must be mentioned; the lack of O,O,O-trimethylthionophosphoric acid ester is, in particular, a characteristic of the process according to the invention. Furthermore, the fact that it is possible to use an aqueous solution of an alkali metal hydroxide, compared with the more expensive alcoholic solutions of an alkali metal alcoholate or alkali metal hydroxide, is a considerable advantage.

The course of the reaction can be represented by the following equation:

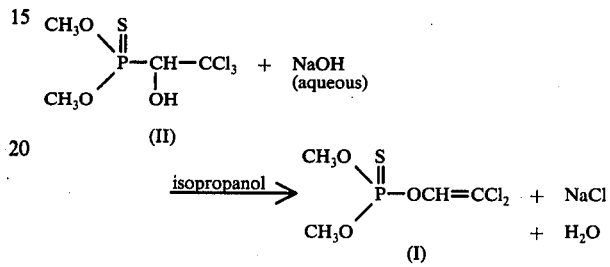

O,O-Dimethyl-1-hydroxy-2,2,2-trichloroethanethionophosphonic acid ester, which is to be used as the starting material, is known (see Belgian Patent Specification No. 839,804).

The process according to the invention can be carried out without the additional use of further solvents since the isopropanol employed has proved to be the optimum reaction medium.

The reaction is, in general, carried out at temperatures of about −20° to +80° C. and preferably of about 0° to 15° C.; it is also generally effected under normal pressure.

When carrying out the process according to the invention, about 1 to 1.05 moles of alkali metal hydroxide in concentrated aqueous solution (about 30 to 50% strength) are preferably employed per mole of O,O-dimethyl-1-hydroxy-2,2,2-trichloroethane-thionophosphonic acid ester. Sodium hydroxide is preferred but potassium and lithium hydroxides, for example, can also be used.

According to a special embodiment, the starting material of the formula (II) can be prepared in the reaction vessel according to Belgian Patent Specification No. 839,804 without the use of a solvent and immediately thereafter, after dilution with isopropanol, reacted, according to the invention, with an aqueous solution of an alkali metal hydroxide.

The compound O,O-dimethyl-O-(2,2-dichlorovinyl)-thionophosphoric acid ester that can be prepared according to the invention is used as an agent for combating pests, above all as an insecticide, especially for plant protection and in the field of hygiene and the protection of stored products.

To the sucking insects there belong, in the main, aphids (Aphididae) such as the green peach aphid (*Myzus persieae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*) the mealy plum aphid (*Hyalopterus arundinis*) and the cherry black-fly (*Myzus cerasi*); in addition, scales and mealybugs (*Coccina*), for example the oleander scale (*Aspidi-*

*otus hederae*) and the soft scale (*Lecanium hesperidum*) as well as the grape mealybug (*Pseudococcus maritimus*); thrips (*Thysanoptera*), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further cicadas, such as *Euscelis bilobatus* and *Nephotettix bipunctatus*.

In the case of the biting insects, above all there should be mentioned butterfly caterpillars (*Lepidoptera*) such as the diamond-back moth (*Plutella maculipennis*), the gipsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

The active compound prepared according to the invention can be converted into the usual formulations, such as solutions, emulsions, suspensions, powders, pastes and granules. These may be produced in known manner, for example by mixing the active compound with extenders, that is to say, liquid or solid or liquefied gaseous diluents or carriers, optionally with the use of surface-active agents, that is to say, emulsifying agents and/or dispersing agents and/or foaming agents. In the case of the use of water as an extender, organic solvents can, for example, also be used as auxiliary solvents.

As liquid diluents or carriers, especially solvents, there are suitable in the main, aromatic hydrocarbons, such as xylene, toluene, benzene or alkyl-naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as dichlorodifluoromethane or trichlorofluoromethane.

As solid carriers there are preferably used ground natural minerals, such as kaolins, clays, talc, chalk, quartz, attapulgite, montmorillonite or diatomaceous earth, and ground synthetic minerals, such as highly dispersed silicic acid, alumina and silicates.

Preferred examples of emulsifying and foam-forming agents include nonionic and anionic emulsifiers, such as polyoxyethylene-fatty acid esters, polyoxyethylene-fatty alcohol esters, for example alkylaryl polyglycol ethers, alkyl sulphonates, alkyl sulphates and aryl sulphonates as well as albumin hydrolysis products; and preferred examples of dispersing agents include lignin sulphite waste liquors and methylcellulose.

The active compound prepared according to the invention can be present in the formulations as a mixture with other active compounds.

In general, the formulations contain from 0.1 to 95 percent by weight of active compound, preferably from 0.5 to 90 percent.

The active compound can be employed as such, in the form of its formulations or in the use forms prepared therefrom, such as ready-to-use solutions, emulsions, foams, suspensions, powders, pastes, soluble powders, dusting agents and granules. They may be used in the customary manner, for example by squirting, spraying, atomising, dusting, scattering, fumigating, gassing, watering, dressing or encrusting.

The active-compound concentrations in the ready-to-use preparations can be varied within fairly wide ranges. In general, they are between 0.0001 and 10%, preferably between 0.01 and 1%, by weight.

The active compound can also be used with good success in the ultra-low-volume (ULV) method where it is possible to apply formulations of up to 95% active compound or even to use the active compound by itself.

The examples which follow illustrate the process according to the present invention.

EXAMPLE 1

94.0 g of 44.7% strength aqueous solution of sodium hydroxide (1.05 mol of sodium hydroxide) were added dropwise to a solution of 273.5 g (1 mol) of O,O-dimethyl-1-hydroxy-2,2,2-trichloroethanethionophosphonic acid ester in 500 g of isopropanol, at an internal temperature of 5° to 10° C., while stirring and with external cooling, and the reaction mixture was stirred for a further 30 minutes in a bath of ice-water. The sodium chloride formed was filtered off and washed twice with 50 g of isopropanol. After the solvent had been distilled off under 12 mm Hg/50° C. bath temperature, the filtrate collected gave a virtually colorless residue which was decanted from a few semi-solid constituents which had flocculated out and freed from the final volatile constituents at 50° C. under reduced pressure (0.01 mm Hg). This gave 222.9 g (94% of theory) of O,O-dimethyl-O-(2,2-dichlorovinyl)-thionophosphoric acid ester in a purity of 96.1% (gas chromatogram). An even higher purity of 99.5% was achieved by a single simple distillation without a column and fractionation heads. The yield was then 215.2 g (90.8% of theory) of O,O-dimethyl-O-(2,2-dichlorovinyl)-thionophosphoric acid ester with a boiling point of 76° C. under a pressure of 2 mm Hg and with a refractive index $n_D^{22}$ of 1.4964.

EXAMPLE 2

(special embodiment)

147.4 g (1 mol) of chloral were added dropwise to a mixture of 126.1 g (1 mol) pf O,O-dimethyl-thionophosphorous acid ester and 2.0 g of triethylamine at a rate such that the heat of reaction could be removed by means of external cooling while maintaining an internal temperature of 15° to 20° C. After a further brief stirring time of 30 minutes at 15° to 20° C., the reaction product, that is to say O,O-dimethyl-1-hydroxy-2,2,2-trichloroethane-thionophosphonic acid ester, was diluted with 500 g of isopropanol; in other respects the procedure was as described in Example 1. This then gave 214.8 g (90.6% of theory via the two stages) of O,O-dimethyl-O-(2,2-dichlorovinyl)-thionophosphoric acid ester in approximately 96% purity or, after simple distillation, 207.4 g (87% of theory via the two stages) in a purity of 99.5%.

It will be appreciated that the instant specification and claims are set forth by way of illustration and not limitation, and that various modifications and changes may be made without departing from the spirit and scope of the present invention.

What is claimed is:

1. A process for the preparation of O,O-dimethyl-O-(2,2-dichlorovinyl)-thionophosphoric acid ester of the formula

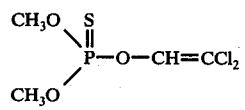

comprising reacting O,O-dimethyl-1-hydroxy-2,2,2-trichloroethanethionophosphonic acid ester of the formula

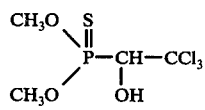

in isopropanol with a concentrated aqueous solution of an alkali metal hydroxide.

2. A process according to claim 1, in which the reaction is carried out at a temperature of about $-20°$ to $+80°$ C.

3. A process according to claim 2, in which the reaction is carried out at a temperature of about $0°$ to $+15°$ C.

4. A process according to claim 1, in which the alkali metal hydroxide solution is of about 30 to 50% concentration and about 1 to 1.05 moles of alkali metal hydroxide are employed per mole of phosphonic acid ester.

5. A process according to claim 1, in which the phosphonic acid ester is formed in situ by the reaction of O,O-dimethyl-thionophosphorous acid ester and chloral and is then reacted without intermediate isolation with the isopropanol solution of the alkali metal hydroxide.

6. A process according to claim 1, in which the alkali metal hydroxide is sodium hydroxide.

7. A process according to claim 5, in which the alkali metal hydroxide is sodium hydroxide, it is employed in about 30 to 50% concentration, about 1 to 1.05 moles of sodium hydroxide being employed per mole of phosphoric acid ester, and the reaction is carried out at a temperature of about $0°$ to $+15°$ C.